(12) United States Patent
Lafferty, IV

(10) Patent No.: US 7,935,086 B2
(45) Date of Patent: May 3, 2011

(54) MULTIPLE DRUG INJECTION APPARATUS

(75) Inventor: John P. Lafferty, IV, Miami Beach, FL (US)

(73) Assignee: L M M Global Innovations, Inc., North Miami, FL (US)

( * ) Notice: Subject to any disclaimer, the term of this patent is extended or adjusted under 35 U.S.C. 154(b) by 240 days.

(21) Appl. No.: 11/610,930

(22) Filed: Dec. 14, 2006

(65) Prior Publication Data

US 2008/0142554 A1 Jun. 19, 2008

(51) Int. Cl.
*A61M 5/00* (2006.01)
(52) U.S. Cl. .......................................... 604/191
(58) Field of Classification Search ............ 604/81, 604/82, 187, 191, 227, 236, 238, 246, 249
See application file for complete search history.

(56) References Cited

U.S. PATENT DOCUMENTS

| | | | | |
|---|---|---|---|---|
| 2,168,686 A * | 8/1939 | Saffir | | 604/415 |
| 3,563,240 A * | 2/1971 | Silver | | 604/87 |
| 4,109,653 A * | 8/1978 | Kozam et al. | | 604/191 |
| 4,367,737 A * | 1/1983 | Kozam et al. | | 604/191 |
| 4,381,778 A * | 5/1983 | Kozam et al. | | 604/191 |
| 4,609,371 A * | 9/1986 | Pizzino | | 604/191 |
| 4,610,666 A * | 9/1986 | Pizzino | | 604/191 |
| 4,915,695 A * | 4/1990 | Koobs | | 604/191 |
| 5,235,862 A * | 8/1993 | Harada | | 73/863.11 |
| 5,354,284 A * | 10/1994 | Haber et al. | | 604/191 |
| 5,411,485 A * | 5/1995 | Tennican et al. | | 604/191 |
| 5,541,515 A * | 7/1996 | Tsujita | | 324/318 |
| 5,553,508 A * | 9/1996 | Dabberdt et al. | | 73/863.02 |
| 5,578,005 A * | 11/1996 | Sancoff et al. | | 604/82 |
| 6,102,897 A * | 8/2000 | Lang | | 604/246 |
| 6,494,861 B1 * | 12/2002 | Tsukernik | | 604/67 |
| 6,508,791 B1 * | 1/2003 | Guerrero | | 604/183 |
| 7,195,610 B1 * | 3/2007 | Flachbart | | 604/99.01 |
| 2006/0178619 A1 * | 8/2006 | Simpkins | | 604/86 |
| 2008/0221602 A1 * | 9/2008 | Kuehner et al. | | 606/167 |

* cited by examiner

*Primary Examiner* — Kevin C Sirmons
*Assistant Examiner* — William Carpenter
(74) *Attorney, Agent, or Firm* — Albert Bordas, P.A.

(57) ABSTRACT

A fluid dispensing device, particularly suited to medicine but also having many other applications. The device selectively dispenses any of one or more fluids contained within the device. Adapters on the dispensing end of the unit permit the device to be effectively used for intra-venous, intra-dermal or intra-muscular injections, gasses, colloids, gels, liquids or other fluids. Adapters on the head of the unit permit the device to be used with or without electrical power and to varying degrees of automatic control for timing, sequence, volume of fluid dispensed and other features.

5 Claims, 16 Drawing Sheets

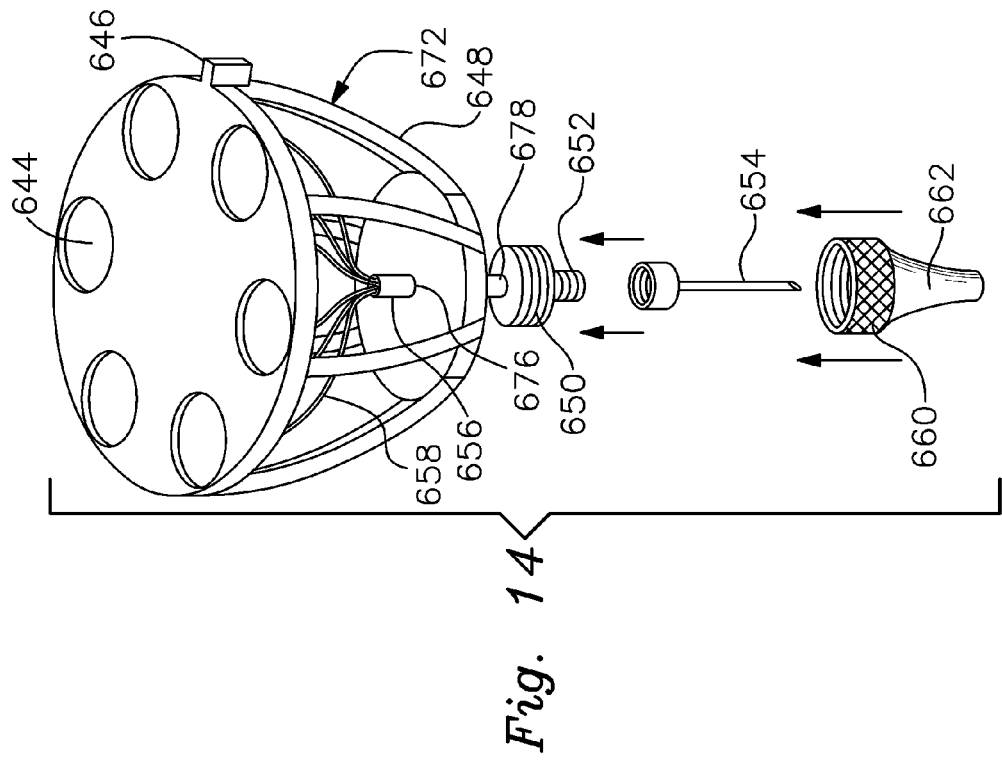
Fig. 14
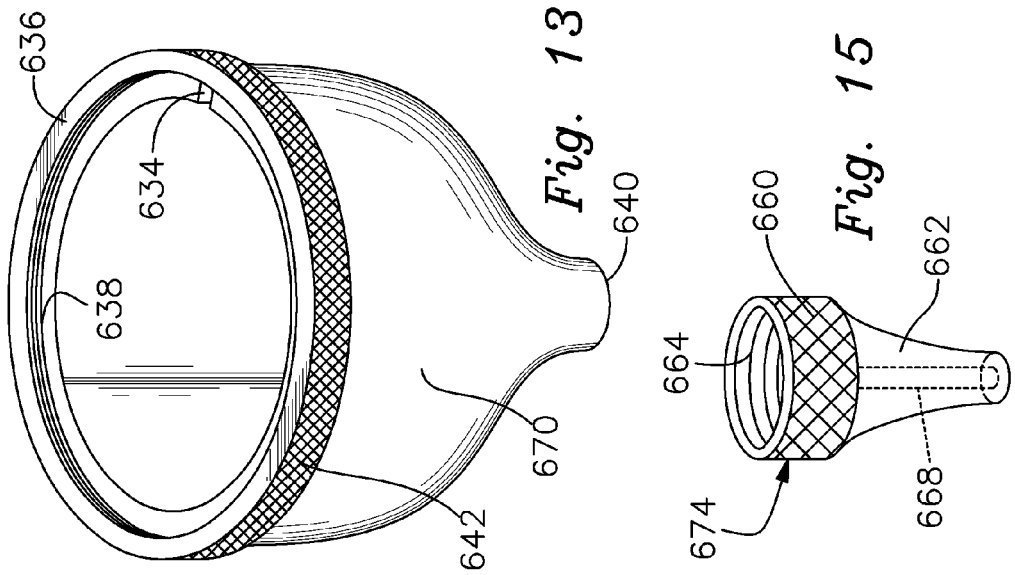
Fig. 13
Fig. 15

MULTIPLE DRUG INJECTION APPARATUS

BACKGROUND OF THE INVENTION

1. Field of the Invention

The present invention relates to a fluid dispenser, and more particularly, to a fluid dispenser that, in one of the preferred embodiments, is suited to dispense drugs.

2. Description of the Related Art

Several designs for fluid dispensers have been designed in the past. None of them, however, includes a means to selectively dispense fluids in a precise volume.

Applicant believes that the closest reference corresponds to U.S. patent application Ser. No. 11/156,575 by inventor Wesley Verkaart. However, it differs from the present invention because the Verkaart invention does not provide a means to precisely dispense liquids, does not have a triggering mechanism, does not provide a means to reduce mixing of the dispensed fluids, has no automatic or electrical features, requires greater user skill when used to deliver drugs and does not provide a means to inject at a specific needle depth, all of which are provided for in the present invention.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a device that contains fluid that can be dispensed quickly.

It is another object of this invention to provide a device that can reduce human error in the dispensing of fluid.

It is an object of this invention to provide a compact and efficient fluid dispensing device.

It is an object of this invention to reduce waste and costs associated with storage and disposal of waste.

It is an object of this invention to provide a device that permits a reduced time to change between fluids dispensed.

It is an object of this invention to permit rapid re-loading of fluid in a safe and efficient manner.

It is an object of this invention to have a device that can dispense various fluids common to a particular application of use.

It is still another object of the present invention to provide a device that can be used effectively and safely, in certain embodiments, for emergency medicine, combat medicine, first responders, anesthesiology, dentistry, veterinary medicine and many medical situations.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 13 is a representation of a perspective view of an embodiment of an apical cap.

FIG. 14 shows an exploded perspective view of an embodiment of an apical cartridge assembly.

FIG. 15 is a perspective view of an embodiment of a guide assembly.

DETAILED DESCRIPTION OF THE PREFERRED EMBODIMENT

Figure 1:
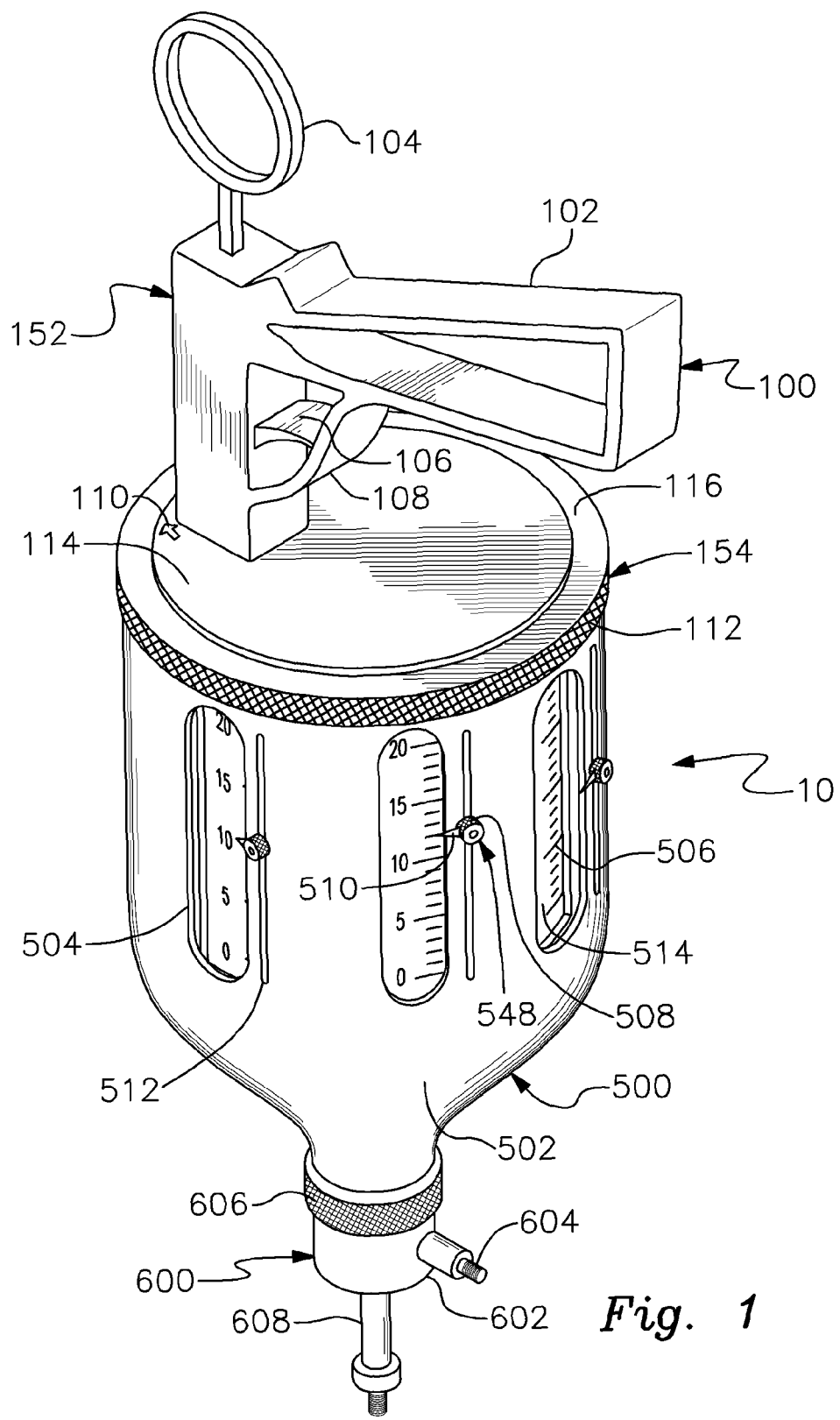
FIG. 1 represents a perspective view of an embodiment of the invention.

Referring now to the drawings, where the present invention is generally referred to with numeral 10, it can be observed in FIG. 1 that in this embodiment it basically includes a manual head assembly 100, a case assembly 500 and an apical assembly 600.

Referring to FIG. 1 an embodiment of said manual head assembly 100 is shown to comprise, inter alia, a handle assembly 152 and a head cap assembly 154. Said handle assembly 152, comprises, inter alia, a handle 102, a cocking lever 104, a trigger 106, a trigger guard 108, an indicator 110.

Said cocking lever 104 is drawn away from said manual head assembly 100 to input energy into the invention to be subsequently used to dispense fluid from the device. Said trigger 106 is depressed to activate the dispensing of a fluid. The trigger 106 is protected from inadvertent activation by the protective trigger guard 108.

Said handle 102 generally conforms to the shape of a human hand to facilitate ergonomic use of the device. As an optional feature, said handle 102 may be open to form a loop that can be used to lighten the device as well as provide a feature to secure the device in storage or while in use. For example, the invention could be hung onto a hook through the handle 102 for storage.

Still referring to FIG. 1, said head cap assembly 154 is comprised of, inter alia, a crown 116 with a knurled grip 112. The handle assembly 152 is rotatably connected to the head cap assembly 154. As described in more detail below, a fluid contained inside the device can be selected for output by applying force to the handle assembly 152 through the handle 102 effecting rotation of the handle assembly 152 relative to the head cap assembly 154. An indicator 110 affixed to a turntable 114 that is part of the handle assembly 152 provides an aid to determine which fluid is selected for dispensing. The knurled grip 112 of the head cap assembly 154 aids the user assemble the device by providing a gripping surface to thread the manual head assembly 100 onto said case assembly 500 thus forming a unitary body.

Yet referring to FIG. 1, said case assembly 500 is comprised of, inter alia, a case 502, one or more viewing ports 504 and a thumb lock assembly 548 that is further comprised of, inter alia, a thumb lock 508, an indicator 510 and a guide 512, each described in more detail below. In one contemplated embodiment, the case assembly 500 contains a vessel 514 that can be partially seen in FIG. 1 through one or more viewing ports 504 to show graduations 506 to determine the volume of fluid contained in the vessel(s) 514.

Again referring to FIG. 1, exterior portions of one of several contemplated embodiments of an apical assembly 600 is shown to comprise, inter alia, an apical cap 602, a fluid port 604, a knurled grip 606 and another fluid port 608, each described in more detail below.

Figure 2:
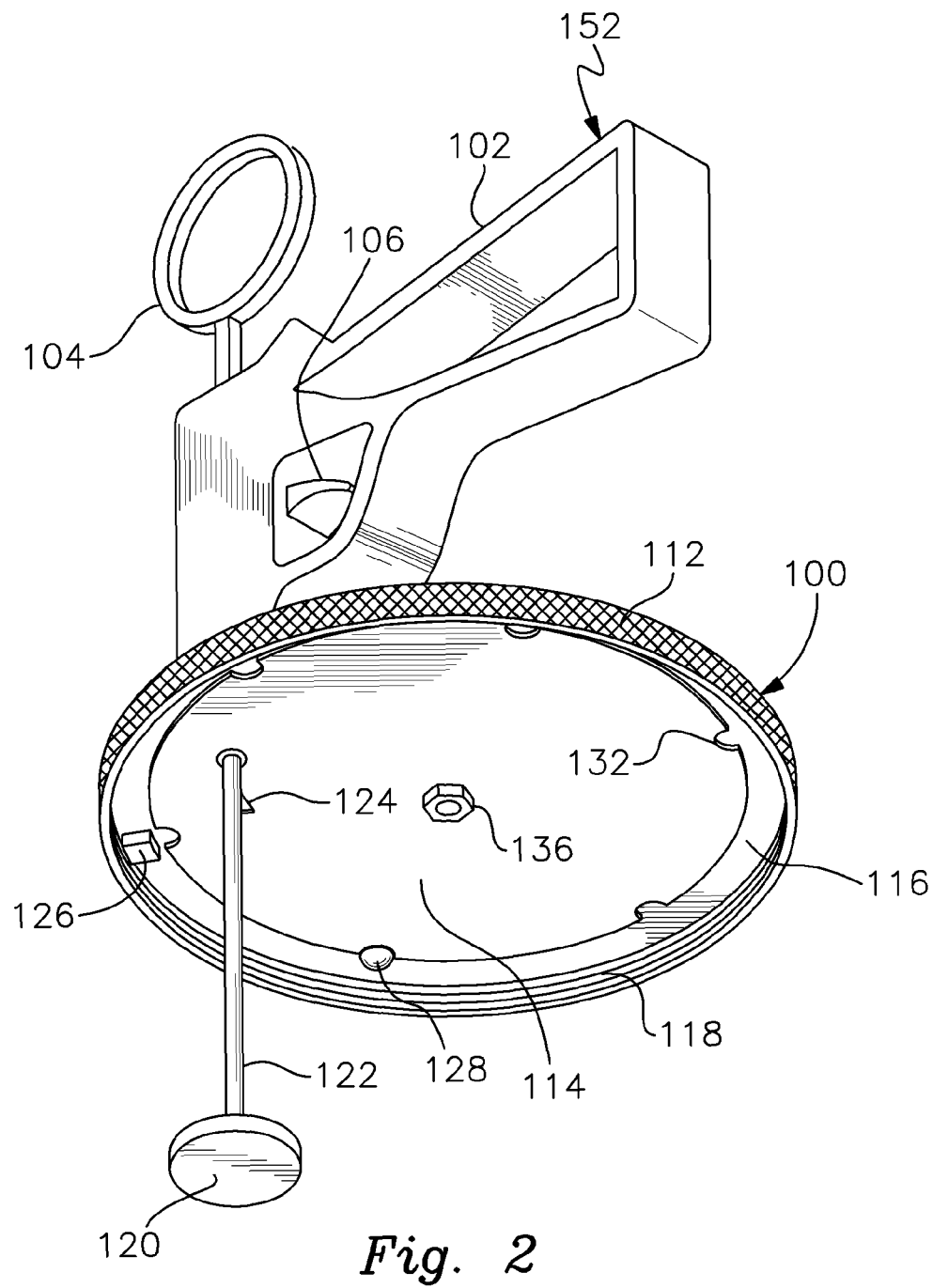
FIG. 2 shows a perspective view of an embodiment of a manual head assembly.

Now referring to FIG. 2 where the underside of the manual head assembly 100 is shown in more detail. In this embodiment of the device the handle assembly 152 is affixed to the turntable 114 by means of a bolt 136, but other means could similarly be used. For example, the handle assembly 152 could be welded to the turntable 114 or be formed from the same unitary material as the turntable 114.

Also shown in FIG. 2 is a knurled grip 112 to provide greater grip when the user assembles or disassembles the device. Threads 118 provide a means to connect the manual head assembly 100 to the case assembly 500. Other means to connect the manual head assembly (or the other head assemblies described below) could include, inter alia, any of a wide variety of known and commonly used clips, snaps, brackets, straps, adhesives, welds, rivets, screws or other similar means. A key 126 is located in a predetermined position superior to the threads 118 and engages into a key slot 530 (shown on FIG. 4) on the case assembly 500 to ensure that the mechanics of the mechanical head assembly 100 align with the case assembly 500 with adequate precision.

Still referring to FIG. 2, a plunger 120 affixed to a shaft 122 is shown. The shaft 122 is movable axially through the turntable 114. Said shaft 122 and plunger 120 are part of the handle assembly 152. One of the handle assembly's 152 functions is to provide a means to move the shaft 122, and thereby the plunger 120, axially through the turntable 114. In this embodiment the shaft 122 also has a stop 124 that interacts with the thumb lock assembly 548 (shown in more detail in FIG. 10 and described below) as one of the contemplated means to regulate the volume of fluid dispensed.

Yet referring to FIG. 2, a spring button 128 and a notch 132, among other components, interact to provide a means to affirmatively select the rotational position of the turntable 114, and thereby the handle assembly 152, relative to the key 126 on the crown 116. As the turntable 114 rotates relative to the crown 116 the spring button 128 encounters and frictionally engages a notch 132. One or more notches 132 are arranged at predetermined positions on the turntable 114 to provide precise alignment of the plunger 120 relative to the key 126. This is but one way to affirmatively select a position. Other suitable means to affirmatively select a position are commonly used in industry.

Figure 3:
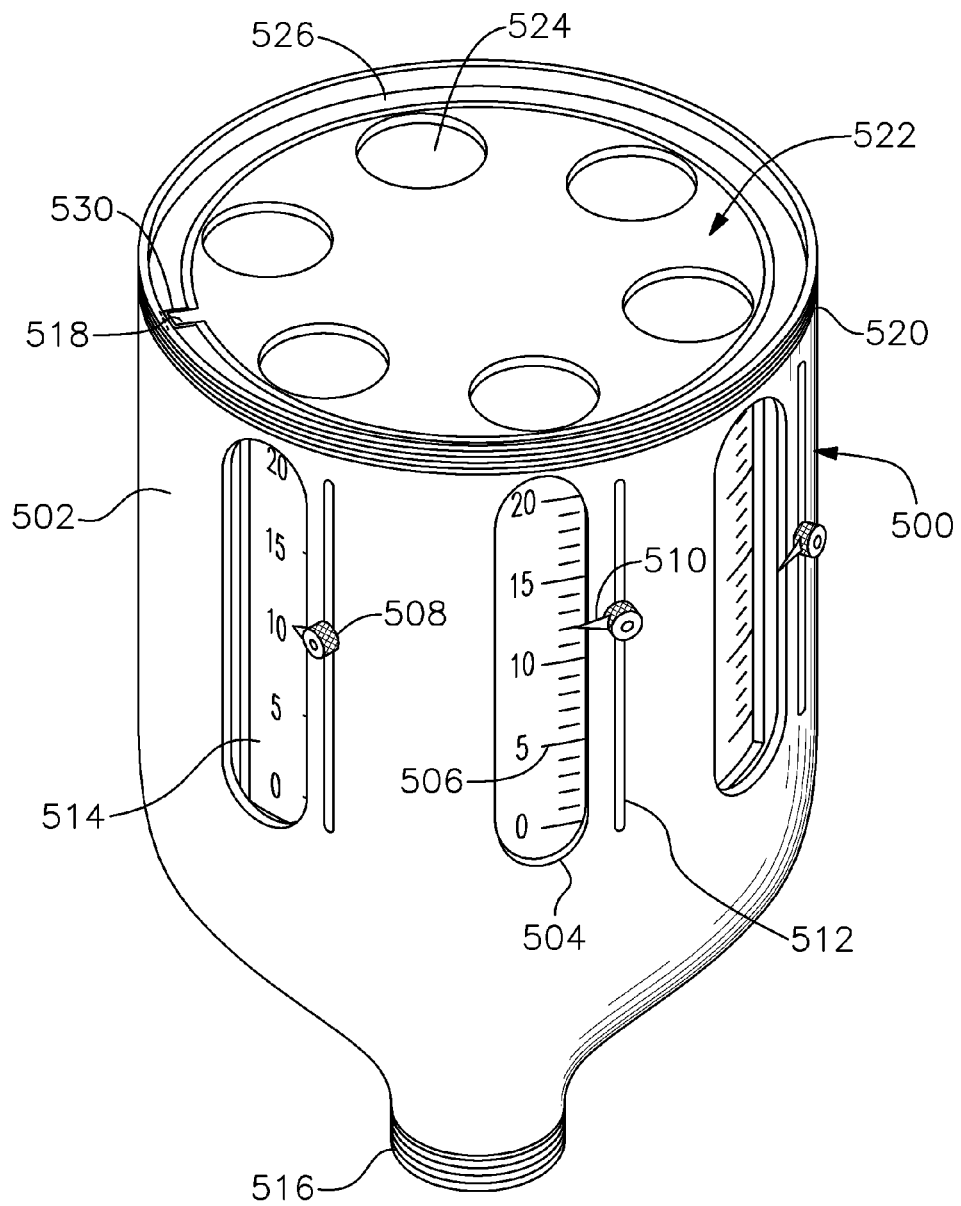
FIG. 3 illustrates a perspective view of an embodiment of a cartridge assembly nested inside a case assembly.

FIG. 3 illustrates one embodiment of the case assembly 500 with a cartridge assembly 522 fitted inside the case assembly 500. In this view of the cartridge assembly a vessel 514, a piston 524 and a key 518 are visible. The vessel 514 is generally cylindrical and is seen through a viewing port 504 on the side of the case assembly 500. The piston 524 is generally cylindrical and slidably engaged inside of the vessel 514. The vessel 514 is sealed by the piston 524. In one contemplated embodiment the vessel 514 and piston 524 is similar to a commonly used medical syringe. When the device is dispensing fluid the plunger 120 (illustrated in FIG. 2) applies force to the surface of the piston 524 and the piston 524 is forced downward axially along the interior of the vessel 514. The key 518 on the cartridge assembly 522 mates with a key slot 530 of the case assembly 500 to ensure proper orientation of the cartridge assembly 522 to the case assembly 500.

Still referring to FIG. 3, some features of the case assembly are visible including, inter alia, the case 502, a seat 526, threads 520, a key slot 530, an indicator 510, a thumb lock 508, a guide 512 and threads 516. The threads 520 engage the threads on the manual head assembly 100 or other embodiments of various head assemblies, infra. Said manual head assembly 100 contacts the case assembly at said seat 526. The threads 516 engage the threads 616 on the apical assembly 600 (shown in FIG. 6) or other embodiments of various apical assemblies, infra.

Figure 4:
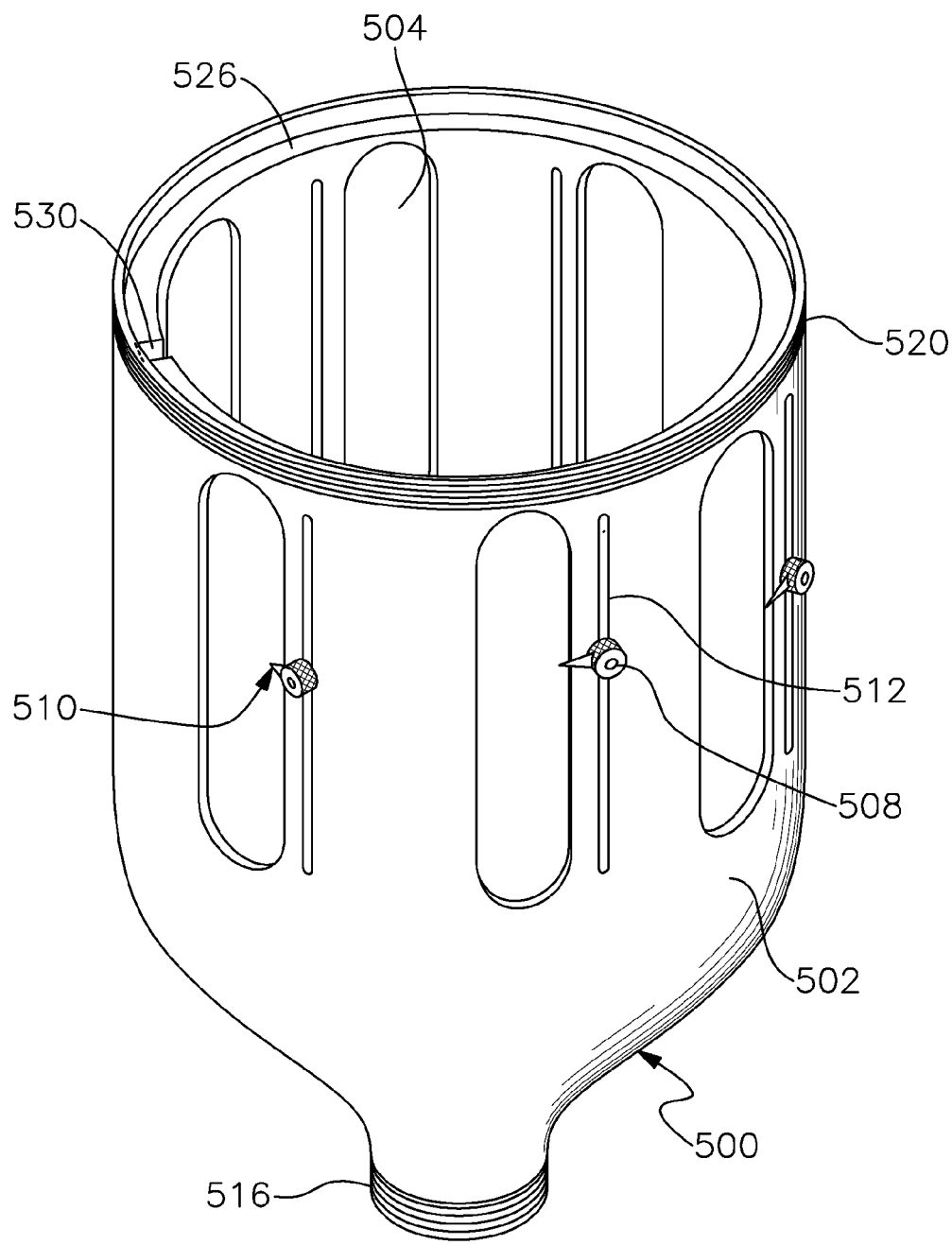
FIG. 4 is a representation of a perspective view of an embodiment of a case assembly.

FIG. 4 depicts the case assembly 500 without the cartridge assembly 522 as is present in FIG. 3. With the cartridge assembly removed the viewing ports 504 are shown around the periphery of the case assembly 500. The number of viewing ports 504 would typically be commensurate with the number of vessels 514 (absent in FIG. 4 and shown in FIG. 5).

Figure 5:
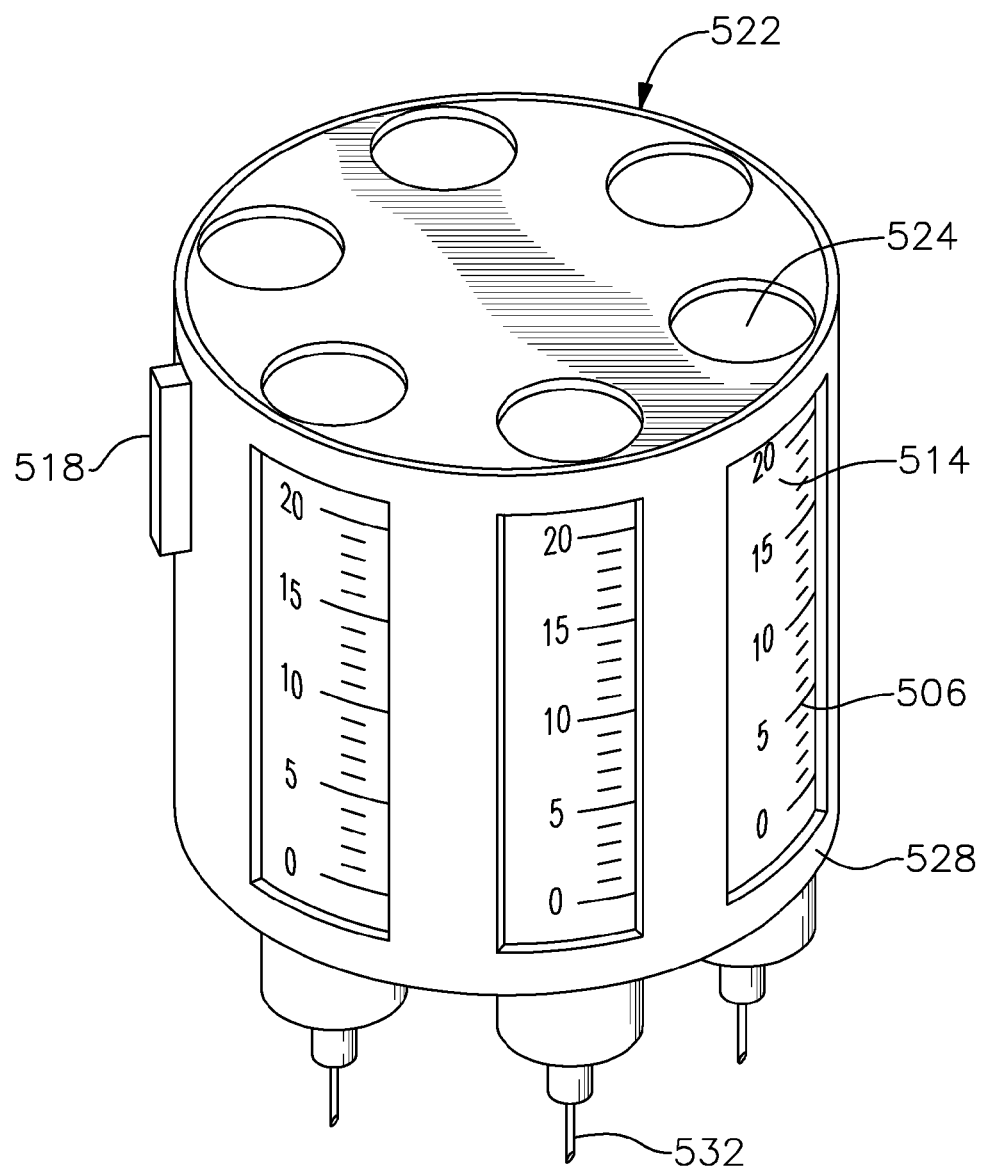
FIG. 5 is a perspective view of an embodiment of a cartridge assembly.

FIG. 5 is an illustration of one contemplated embodiment of a cartridge assembly 522 that comprises, inter alia, a frame 528, a vessel 514, graduations 506, piston 524, vessel port 532 and key 518. Said frame 528 provides the structure to hold one or more vessels 514 fixed relative to one another. Said key 518 is positioned at a predetermined location on the frame 528 and is dimensioned to engage the key slot 530 on the cartridge assembly 522 (shown on FIG. 4) at a precise relative orientation. An optional, but desirable, feature on each vessel 514 are graduations 506 to aid the user to more precisely measure the volume of fluid dispensed. Generally, the graduations 506 are readable through a viewing port 504 (as shown in FIG. 3). The graduations 506 would typically show the remaining volume of fluid contained in the vessel 514 in milliliters or cubic centimeters as indicated by reading the position of the bottom of the piston 524 relative to the graduations 506. Said vessel port 532 is the path by which the fluid contained in the vessel 514 exits the vessel 514 during dispensing. Vessel port 532 can also be where fluid is drawn back into the vessel 514 when refilling the vessel 514. In one of the preferred embodiments the vessel 514 is a common syringe and the vessel port 532 is a common hypodermic needle affixed to the lower end of the vessel 514.

Figure 6:
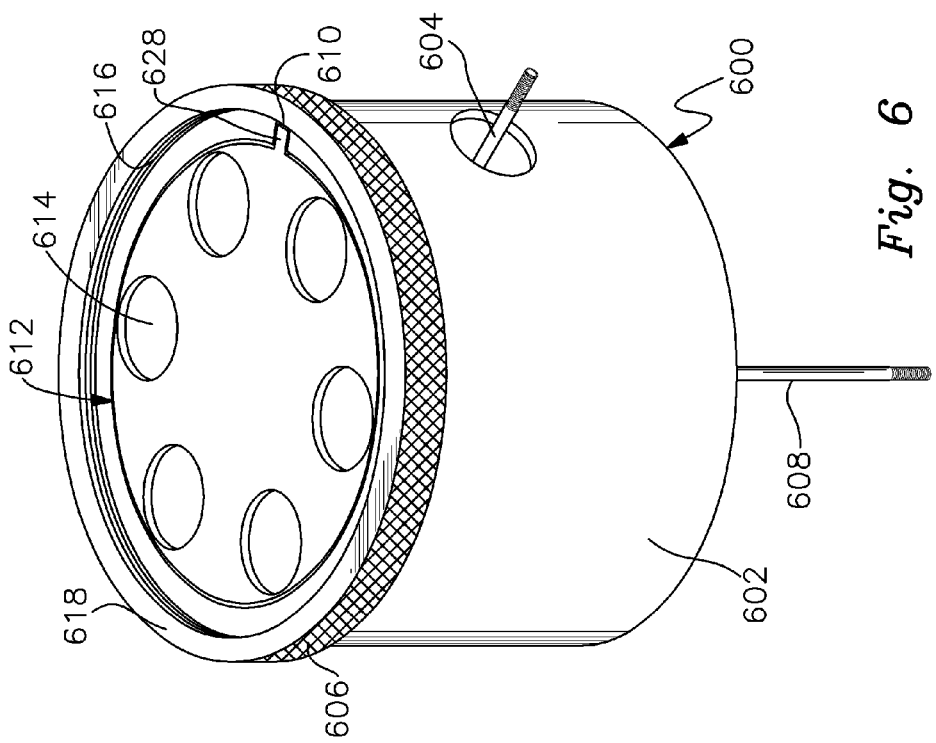
FIG. 6 is a perspective view of an embodiment of an apical cartridge assembly nested inside an apical assembly.

Referring now to FIG. 6 where one of the embodiments of an apical assembly 600 is shown that is comprised of, inter alia, an apical cap 602, a fluid port 604, a knurled grip 606, a fluid port 608, a key slot 610, a septum 614, threads 616, a seat 618 and an apical cartridge assembly 612. When in typical use said apical assembly 600 is threaded onto the case assembly 500 by means of threads 616 on the apical assembly 600 engaging the threads 516 on the case assembly 500 and rests on the seat 618. A knurled grip 606 aids the user when threading the pieces together. Other contemplated means to secure the case assembly 500 to the apical assembly 600 (or other embodiments of apical assemblies) could include, inter alia, any of a wide variety of known and commonly used clips, snaps, brackets, straps, adhesives, welds, rivets, screws or other similar means.

Still referring to FIG. 6, the apical cartridge assembly 612 is nested in the apical assembly 600. The orientation of the apical cartridge assembly 612 with the apical cap 602 is maintained by aligning a key 628 on the apical cartridge assembly 612 in the key slot 610 on the apical assembly 600. The top of the apical cartridge assembly 612 may have a septum 614 capable of receiving said vessel port 532 (shown in FIG. 5) and making a leak resistant union. For example, if the vessel port 532 was similar in form to a common hypodermic needle then the septum 614 could be made of a rubber-like material that a hypodermic needle could readily puncture and maintain a leak-resistant seal. Other means to connect the apical cartridge assembly 612 to cartridge assembly can be easily improvised from a wide variety of medical and industrial connectors readily available.

Figure 7:
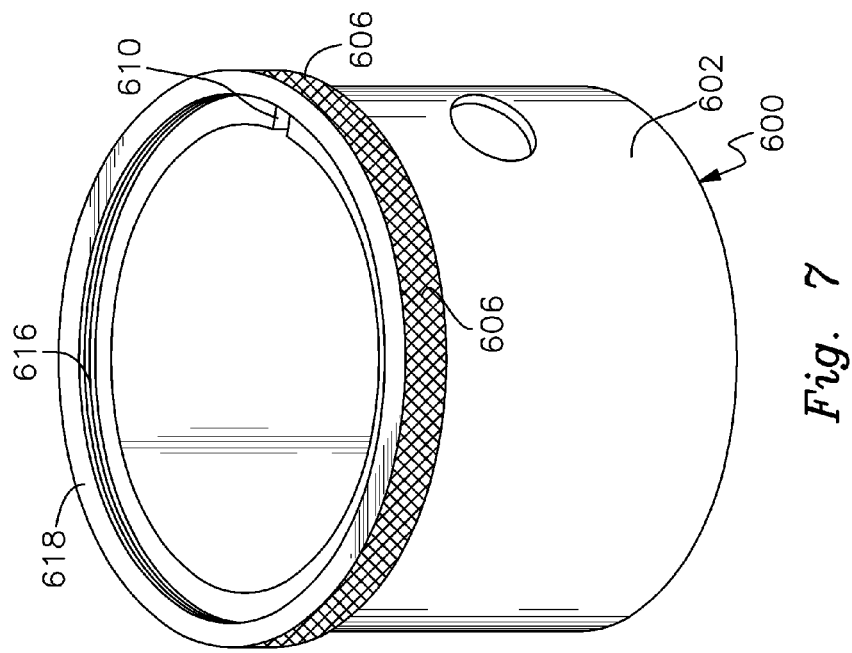
FIG. 7 illustrates a perspective view of an embodiment of an apical assembly without a cartridge assembly.

FIG. 7 shows an embodiment of the apical assembly 600 without the apical cartridge assembly 612. Shown in this view is, inter alia, the knurled grip 606 to give the user better grip when attaching the apical assembly 600 to the case assembly 500 by means of the threads 616 on the apical assembly 600 and the threads on the case assembly 516. Other contemplated means to secure the case assembly 500 to the apical assembly 600 (or other embodiments of an apical assembly) could include, inter alia, any of a wide variety of known and commonly used clips, snaps, brackets, straps, adhesives, welds, rivets, screws or other similar means. A seat 618 provides a stable surface for the case assembly 500 to contact the apical assembly 600.

Figure 8:
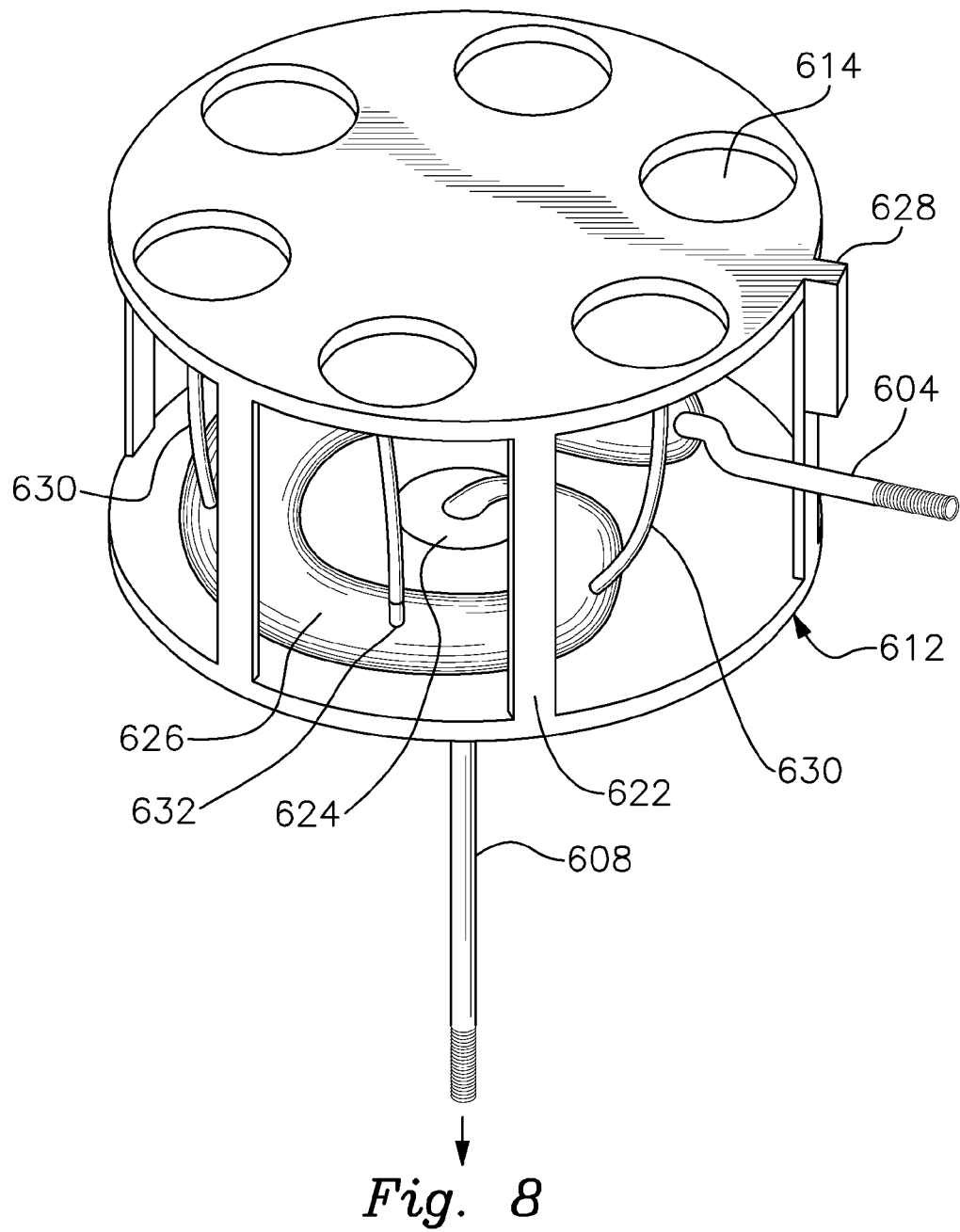
FIG. 8 shows a perspective view of an embodiment of an apical cartridge assembly.

FIG. 8 is an illustration of one embodiment of an apical cartridge assembly 612 removed from the apical cap 602 (shown in FIG. 7). The structure of the apical cartridge assembly 612 is supported by a frame 622. On the superior side of said frame is one or more septa 614. Typically, one septum 614 would be provided for each vessel 514 (shown on FIG. 5). Each vessel port 532 on the cartridge assembly 522 mates with the corresponding septum 614 on the apical cartridge assembly 612 to form a pressure-resistant seal. In one embodiment the vessel port 532 is similar to a hypodermic needle and the septum 614 is a rubber-like material and when the vessel port 532 is mated with the septum 614 the hypodermic needle pierces the rubber-like material creating a pressure-resistant union. Other suitable means of connecting the cartridge assembly 522 to the apical cartridge assembly 612 have been considered and may include, inter alia, clips, nipples, clamps and other connectors.

Still referring to FIG. 8, in this embodiment each septum 614 is integrally connected to a conduit 630 that conducts the fluid to an apical chamber 626. The apical chamber 626 is generally hollow and has a predetermined interior volume specific to the application. For example, in some applications it is preferable to avoid commingling of the various fluids as they are dispensed in succession and therefore a minimal volume is desired. In other applications a greater volume of the apical chamber and/or an agitator inside the apical chamber 626 may be desired to promote mixing of the fluids as the fluids are dispensed. Optionally, a valve 632 that prevents back-flow of fluid into the conduit 630 is inserted between all or each conduit 630 and the apical chamber 626. A key 628 may be used to ensure consistent orientation of the apical cartridge assembly 612 with the apical cap 602 when engaged into key slot 610. A port 624 in the frame 622 provides an egress for the fluid port 608.

In the embodiment of the apical cartridge assembly 612 demonstrated in FIG. 8 there is a fluid port 604 that receives fluid from a source external to the device and a fluid port 608 where any fluids finally exit the device. One of the contemplated applications that this embodiment of the apical cartridge assembly would be well suited is for intra-venous injections. In this application it is possible that the fluids, in this example drugs, dispensed should not be mixed or commingle. To remedy this potential issue a sterile saline solution source can be connected to the fluid port 604. After or as one of the drugs is delivered from the vessel 514, through the vessel port 532, septum 614 and conduit 630 into the apical chamber 626 the sterile saline solution is introduced through the fluid port 604 to flush the drug out of the apical chamber 626 and through a fluid port 608 where the drug exits the device and is pushed toward a patient by the sterile saline flow.

Figure 9:
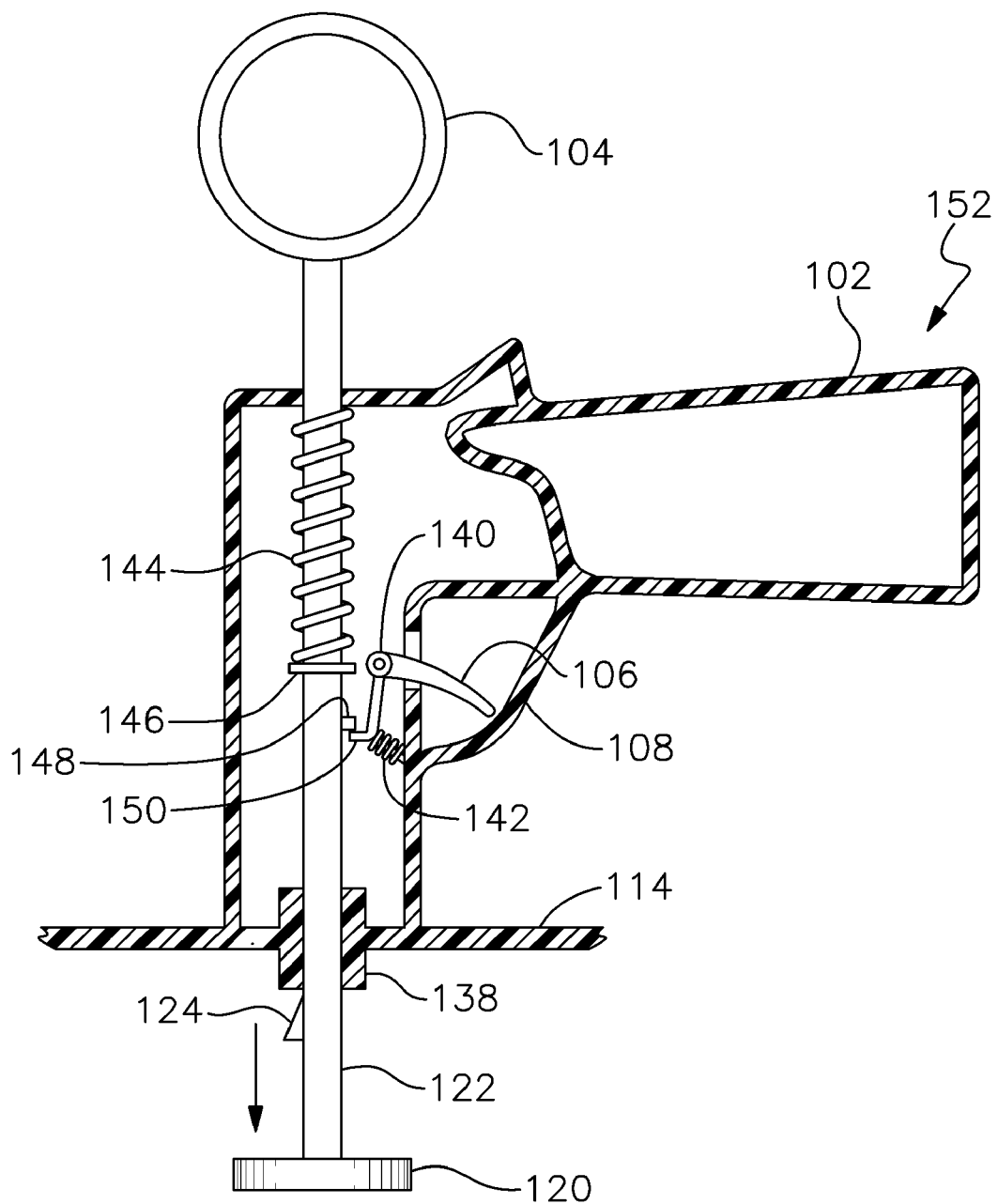
FIG. 9 is a representation of a cross-sectional view of an embodiment of a manual head assembly.

FIG. 9 is a cross-sectional view of the handle assembly 152 and shows an embodiment of the internal components of the manual head assembly 100. This embodiment comprises, inter alia, a handle 102, a cocking lever 104, a trigger 106, a trigger guard 108, a turntable 114, a plunger 120, a shaft 122, a stop 124, a guide 138, a fulcrum 140, a spring 142, a spring 144, a stop 146, a stop 148 and a catch 150. When preparing the device for use the user manually pulls on the cocking lever 104 to compress the spring 144 that is held in place on the shaft 122 by the stop 146. When the spring 144 is adequately compressed the catch 150 contacts the stop 148 to hold the spring 144 under compression. The catch 150 is biased toward and engages the stop 148 by means of a spring 142. When the user desires to dispense a fluid the trigger 106 is pulled and the trigger pivots at the fulcrum 140, compresses the spring 142 and the catch 150 clears the stop 148 freeing the spring 144 to push against the stop 146 and thereby push the shaft 122 and plunger 120. The force of the spring 144 is transferred to the piston 524 (shown in FIG. 5) to initiate dispensing a fluid contained in the vessel 514 (shown in FIG. 5). The shaft 122 maintains axial alignment by means of a guide 138. A trigger guard 108 is provided to prevent inadvertently pressing the trigger 106.

Figure 10:
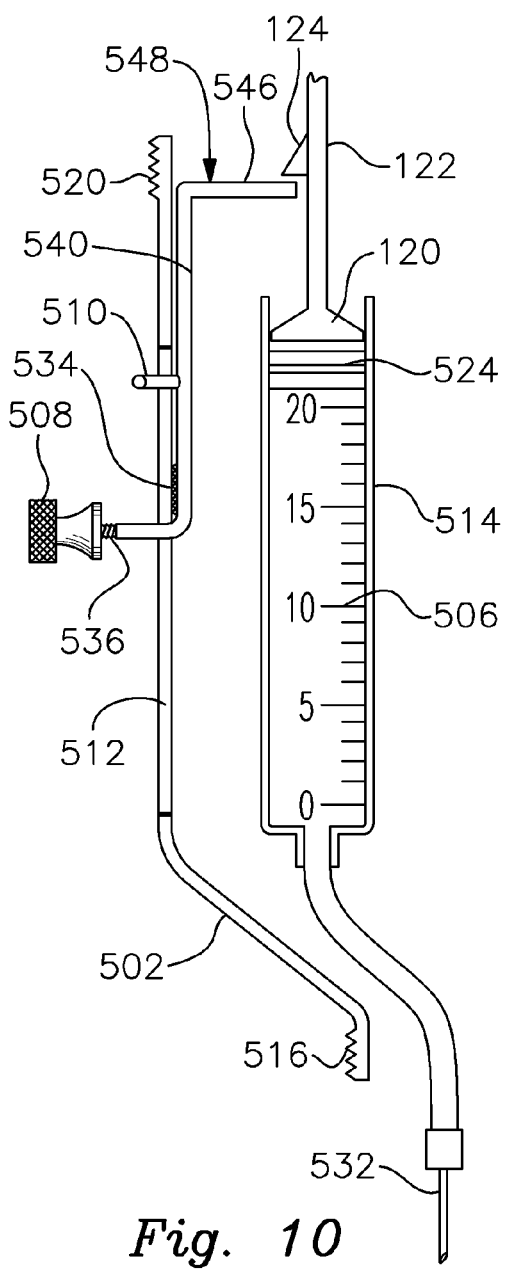
FIG. 10 is a partial cross-sectional view showing an embodiment of case assembly.
Figure 11:
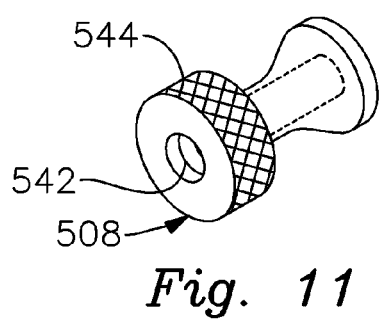
FIG. 11 shows a perspective view of an embodiment of a thumb lock.
Figure 12:
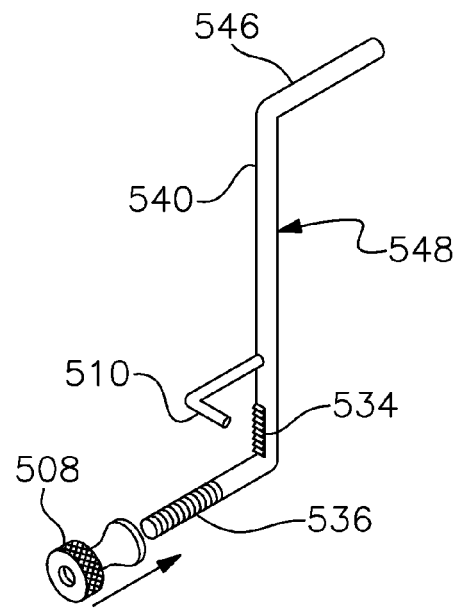
FIG. 12 is a perspective view of an embodiment of a thumb lock assembly.

FIGS. 10, 11 and 12 show in more detail one of the embodiments of the thumb lock assembly 548 that is utilized to limit the travel of the piston 524 effectively stopping the dispensing of fluid. In this embodiment of the device the thumb lock assembly comprises, inter alia, a rod 540, an indicator 510, a stop 546, teeth 534, thumb lock 508, threads 536 and threads 542. The indicator 510, thumb lock 508 and threads 536 are outside of the case 502 while the stop 546, rod 540 and teeth 534 are inside the case 502 for normal operation. The thumb lock 508 has internal threads 542 corresponding to threads 536 on the rod 540. When the thumb lock assembly 548 is locked the thumb lock 508 is threaded onto threads 536 and the thumb lock 508 contacts the exterior of the case 502 while the teeth 534 contact the interior of the case 502 with such firmness as to prevent movement of the thumb lock assembly 548 relative to the case 502. A knurled grip 544 on the thumb lock 508 may be provided to improve the users grip on the thumb lock 508. To adjust the thumb lock assembly 548 the thumb lock 508 is loosened and the thumb lock assembly 548 is freed to travel along the guide 512, also shown in FIG. 4. The indicator 510 can be viewed by the user on the exterior of the case 502 adjacent to the viewing port 504. When the thumb lock assembly 548 is locked and the plunger 120 is in motion dispensing fluid and the piston 524 has traveled to the point indicated by the indicator 510 the stop 124 on the shaft 122 contacts the stop 546 on the thumb lock assembly 548 preventing the shaft 122 and plunger 120 from traveling further thus stopping dispensing more fluid. The dimensions of the thumb lock assembly 548 are such that when the indicator 510 is adjacent to the graduations 506 seen through the viewing port 504 the piston 524 will not travel further than the indicated level inside the vessel 514.

FIG. 13 shows another alternative embodiment of an apical cap 670 with features that are comprised of, inter alia, a key slot 634, a seat 636, threads 638, a knurled grip 642 and a port 640. This embodiment is attached to the case assembly 500 by means of threads 638 screwed onto threads 516 with the assistance of the knurled grip 642 until the seat 636 contacts the case 502. As alternatives to the threads 638 the apical cap 670 could be attached to the case 502 by many commonly available means such as clips, welds, adhesives, brackets or other means. A key slot 634 ensures proper alignment of the apical cap 670 relative to an apical cartridge assembly 672 (shown in FIG. 14).

FIGS. 14 and 15 depict an embodiment of an apical cartridge assembly 672 removed from the apical cap 670. The apical cartridge assembly 672 is generally supported by a frame 648. On the superior side of said frame is one or more septa 644. Typically, one septum 644 would be provided for each vessel 514 (shown on FIG. 5). Each vessel port 532 on the cartridge assembly 522 mates with the corresponding septum 644 on the apical cartridge assembly 672 to form a pressure-resistant seal. In one embodiment the vessel port 532 is similar to a hypodermic needle and the septum 644 is a rubber-like material and when the vessel port 532 is mated with the septum 644 the hypodermic needle pierces the rubber-like material creating a pressure-resistant union. Other suitable means of connecting the cartridge assembly 522 to the apical cartridge assembly 672 have been considered and may include, inter alia, clips, nipples, clamps and other connectors.

Still referring to FIGS. 14 and 15, in this embodiment each septum 644 is integrally connected to a conduit 658 that conducts the fluid to an apical chamber 656. The apical chamber 656 is generally hollow and has a predetermined interior volume specific to the application. For example, in some applications it is preferable to avoid commingling of the various fluids as they are dispensed in succession and therefore a minimal volume is desired. In other applications a greater volume of the apical chamber and/or an agitator inside the apical chamber 656 may be desired to promote mixing of the fluids as the fluids are dispensed. Optionally, a valve that prevents back-flow of fluid into the conduit 658 is inserted between all or each conduit 658 and the apical chamber 656. A key 646 may be used to ensure consistent orientation of the apical cartridge assembly 672 with the apical cap 670 when the key 646 is engaged into key slot 634. A port 676 in the frame 648 provides an egress for a conduit 678. On said conduit 678 are threads 652 and threads 650. Threads 652 extend below and have a smaller diameter than the threads 650. A needle 654 or other delivery device is threaded onto the threads 652 on the conduit 678. A guide assembly 674 comprised of, inter alia, a knurled grip 660, a guide 662, threads 664 and a shaft 668 is placed over the needle 654 and threaded via threads 664 onto threads 650. The guide assembly 674 can be threaded onto threads 650 to varying depths thus exposing more or less of the tip of the needle 654. This feature controls the precise depth that the needle 654 can penetrate, for example into a patient.

One of the contemplated applications that this embodiment of the apical cartridge assembly would be well suited for is for intra-dermal or intra-muscular injections. In this application it is not typically suitable to utilize a flushing saline solution as described above for the apical cartridge assembly 612 shown in FIG. 8 because too great a volume of fluid would be dispensed under the skin or into the muscles of the patient. In this embodiment of the apical cartridge assembly 672 it may be preferred to have minimum interior volume of the apical chamber 656.

Figure 16:
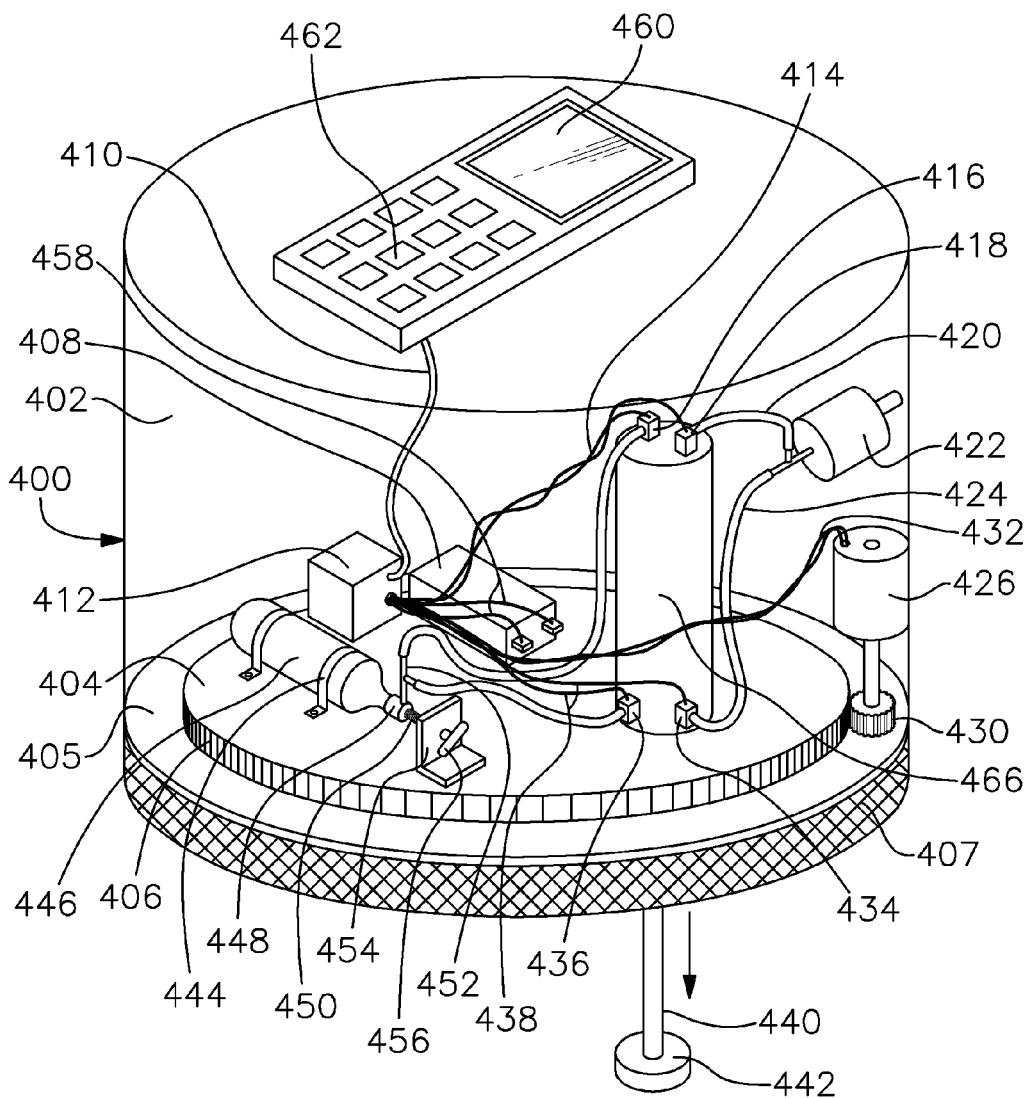
FIG. 16 is a representation of a perspective view of an embodiment of a pneumatic powered head assembly.

Now referring to FIG. 16 where an embodiment of a pneumatic head assembly 400 is shown. The pneumatic head assembly is housed in a case 402 made of a durable material to provide structure and protection for the contents of the case 402. A base 405 is affixed to the bottom side of the case 402. A threaded ring 407 with knurled edges is at the base of the case 402 and is used to thread the pneumatic head assembly 400 to the case assembly 500 at threads 520 (shown in FIG. 3). A turntable 404 is in the interior of the case 402 and is rotatable relative to the base 405. The turntable 404 has a plurality of teeth 406 around its periphery. The force for rotating the turntable 404 is provided by a motor 426 connected to a gear 430. The gear 430 engages the teeth 406 thereby transferring the force of the motor 426 to cause a rotation of the turntable 404 relative to the base 405. A variety of types of gears have been contemplated that would be equally effective alternative for gear 430 that include, inter alia, a worm-type gear if the axis of the motor 426 is perpendicular to the axis of the turntable 404 or a traditional circular gear if the axis of the motor 426 is parallel to the axis of the turntable 404. The motor 426 is connected to the CPU 412 by a cable 432. In the preferred embodiment of the pneumatic head assembly 400 the motor 426 is a stepping motor.

The motor 426 and the rest of the pneumatic head assembly 400 can be controlled by a CPU 412 (central processing unit) that is powered by a battery 408 or other power source such as regular alternating current, photo-voltaic cells, fuel cells or any other available power source. The battery 408 is connected to the CPU 412 by wires 458. The CPU 412 receives input from an input device 462 that may be comprised of, for example, a keypad, buttons, knobs, dials or any other input means. The CPU 412 is connected to the input device 462 by a cable 410.

Optionally, the CPU 412 may also utilize a display 460 to show the user relevant information as to the operation of the device. For example, the display 460 could show the user a variety of menus to aid in programming the CPU 412 for a particular purpose, the status of the device, time, pressure, volume of fluid remaining or dispensed by the device, battery power, identification of fluid or any of a wide variety of information relevant to the user of the device. The CPU 412 is connected to the display 460 by a cable 410 or other means.

The CPU 412 may also control, inter alia, a valve 416, a valve 418, a valve 434 and a valve 436 each mounted onto a cylinder 466. Valve 416 and valve 418 are connected to the CPU 412 by a cable 414. Valve 434 and valve 436 are connected to and controlled by the CPU 412 through cable 438. Valve 416, valve 418, valve 434 and valve 436 control pressurized fluid passing into and out of the interior of the cylinder 466.

In one of the preferred embodiments of the pneumatic head assembly 400 a pressure vessel 446 is secured by a mount 444 onto the turntable 404. The pressure vessel 446 is connected to a receiver 448 and held into place by a tap 450 that is in turn secured by a mount 454. A handle 456 aids the user in securing the tap 450 to the pressure vessel 446 creating a pressure resistant seal. A conduit 452 carries fluid under pressure to valve 416 and valve 436. A conduit 420 is connected to valve 418 and provides a pathway for exhaust to escape out of the cylinder 466 and exit the device through a muffler 422. A conduit 424 is connected to valve 434 and provides a pathway for exhaust to escape out of the cylinder 466 and exit the device through the muffler 422. In the preferred embodiment the pressure vessel 446 is a common carbon dioxide cartridge such as are commonly used in pellet guns.

Still referring to FIG. 16, an alternate embodiment of the pneumatic head assembly 400 consists of, inter alia, substituting a hydraulic pump (not depicted) instead of the pressure vessel 446. The hydraulic pump is controlled by CPU 412 and powered by a battery 408. Conduit 452 carries hydraulic fluid to valve 416 and valve 436.

Figure 17:
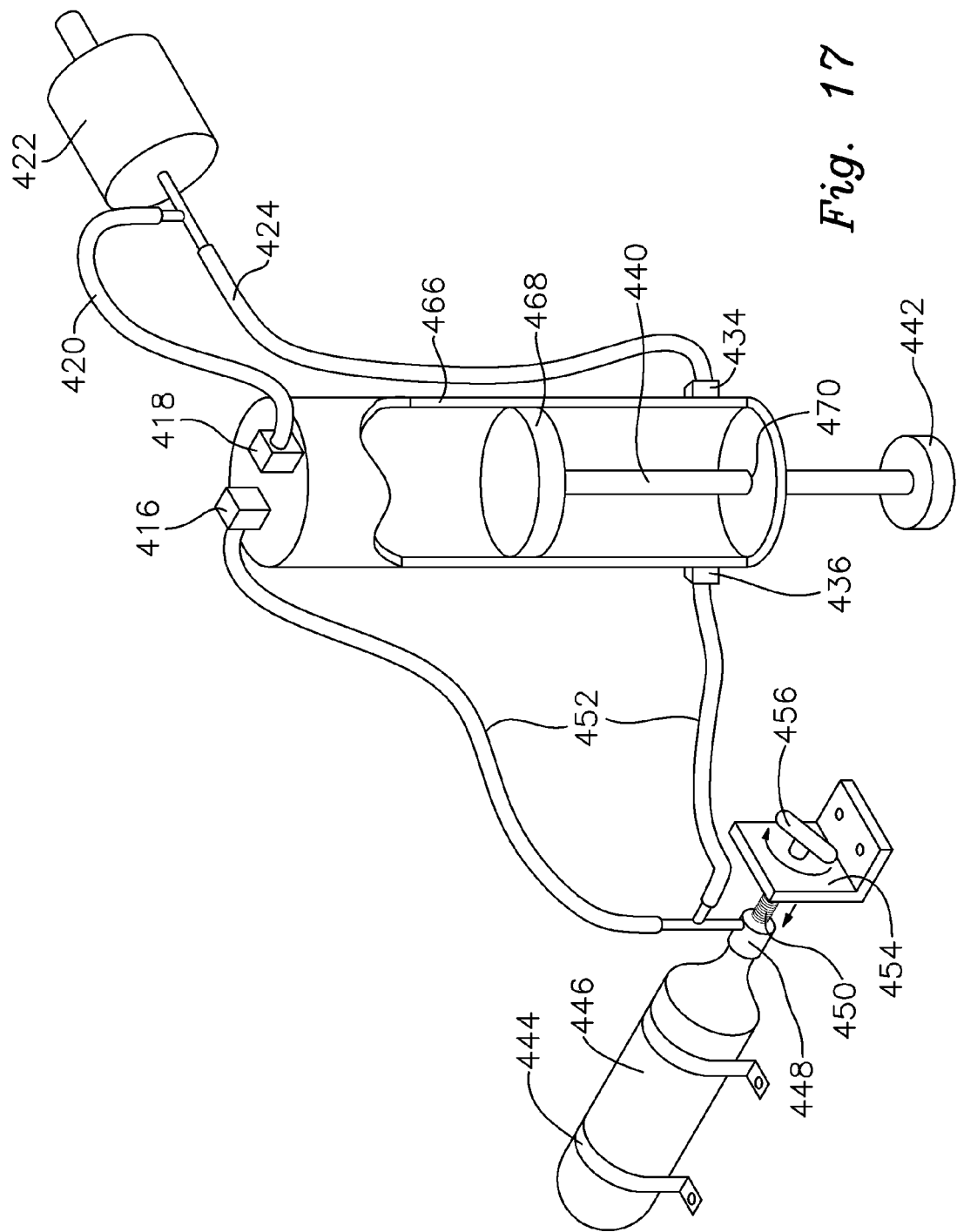
FIG. 17 shows a perspective view of a partial cross-section of an embodiment of a pneumatic head assembly.

Now referring to FIG. 17 where a partial cutaway view of an embodiment of the pneumatic head assembly 400 (as shown in FIG. 16) showing a cross section of said cylinder 466. Said pressure vessel 446 is mounted securely by said mount 444 to said turntable 404. Said tap 450 is secured to the turntable 404 by mount 454. Said conduit 452 is secured to the pressure vessel 446 at the receiver 448 to form a pressure resistant seal by tightening the handle 456 thereby securing the union between the receiver 448 and the pressure vessel 446.

Still referring to FIG. 17, on the interior of the cylinder 466 is a piston 468 connected to a shaft 440 that passes though the floor of the cylinder 466 at a seal 470 and terminates in a plunger 442 that retractably extends through and below said turntable 404. To move the plunger 442 down, the valve 416 is opened and valve 418 is closed thereby permitting the fluid in the pressure vessel 446 to flow through the conduit 452 into the cylinder 466 creating high pressure above the piston 468 while at the same time valve 436 is closed and valve 434 opens so that the volume inside the cylinder 466 below the piston 468 is open to ambient pressure through the conduit 424 and muffler 422. To raise the plunger 442 the inverse must occur: the valve 436 is opened and valve 434 is closed thereby permitting the fluid in the pressure vessel 446 to flow through the conduit 452 into the cylinder 466 creating high pressure below the piston 468 at the same time valve 416 is closed and valve 418 opens the volume inside the cylinder 466 above the piston 468 to ambient pressure through the conduit 420 and muffler 422.

Returning now to FIG. 16 this embodiment of a pneumatic head assembly 400 is typically used in conjunction with a case assembly 500 as shown in FIG. 3 and an apical assembly 600 as shown in FIG. 6. Both the pneumatic head assembly 400 and apical assembly 600 are connected to the respective ends of the case assembly 500 to form a single unit. When the device is used the plunger 442 comes into contact with the piston 524 on the top of the vessel 514 and pushes any fluid contained in the vessel 514 out of the device through the apical assembly 600.

Figure 18:
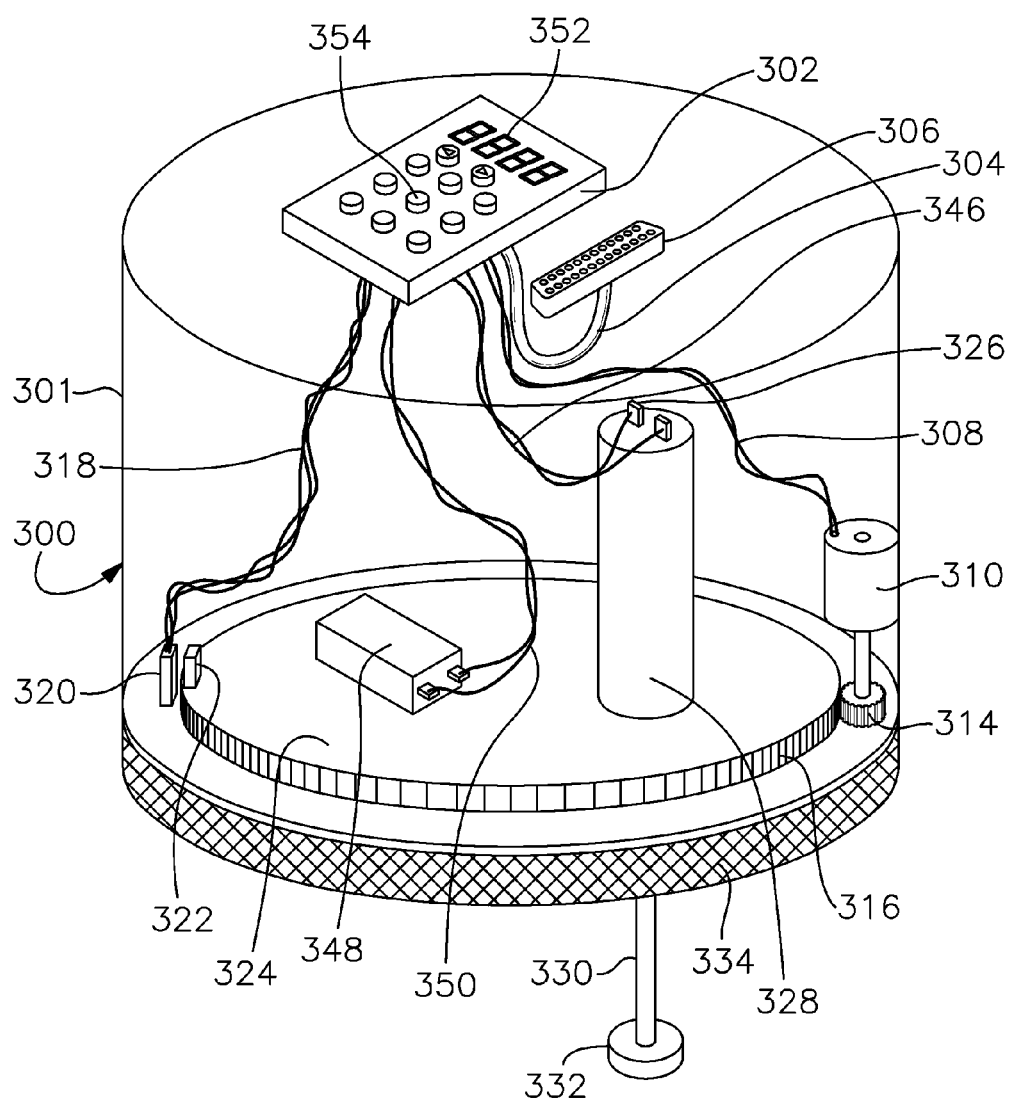
FIG. 18 illustrates a perspective view of an embodiment of an electronic head assembly.

Now referring to FIG. 18 where an embodiment of an electronic head assembly 300 is shown. The structure of the electronic head assembly 300 is provided by a case 301. At the base of said case 301 is a threaded ring 334 that is used to connect the electronic head assembly 300 to a case assembly 500 at threads 520 (shown on FIG. 3). The electronic head assembly 300 is controlled by a central processing unit 302 (CPU) and powered by a battery 348 and connected to said battery 348 by a cable 350. The CPU 302 has an input device 354 that serves as an interface between the user and the invention. The input device 354 may consist of, inter alia, a keypad, dials, buttons or other similar means. The CPU 302 is also connected to a display 352 such as a liquid crystal display (LCD), light emitting diodes (LED) or other suitable means of display that are commonly used. The display 352 shows information to the user such as status, programs, power supply, fluid dispensed or remaining and any other relevant information. A socket 306 is optionally present and provides a means to connect a computer device to control, program or monitor said CPU 302. Said socket 306 is connected to said CPU 302 by a cable 304

Said CPU 302 is connected to a motor 310 by a cable 308. Said motor 310 is connected to a gear 314 that interfaces with teeth 316 around the circumference of a turntable 324. Said CPU 302 controls and activates said motor 310 that in turn rotates said gear 314 that in turn rotates said turntable 324 about its axis. In the preferred embodiment said motor 310 is a stepping motor.

Still referring to FIG. 18, in a preferred embodiment a lineal actuator 328 is fixed onto said turntable 324. Said lineal actuator 328 extends and retracts a shaft 330 that terminates in plunger 332 extendable below said turntable 324. Said lineal actuator 328 is controlled by said CPU 302 and is connected to said CPU 302 by cable 346 connected to terminals 326 on the lineal actuator 328.

Figure 19:
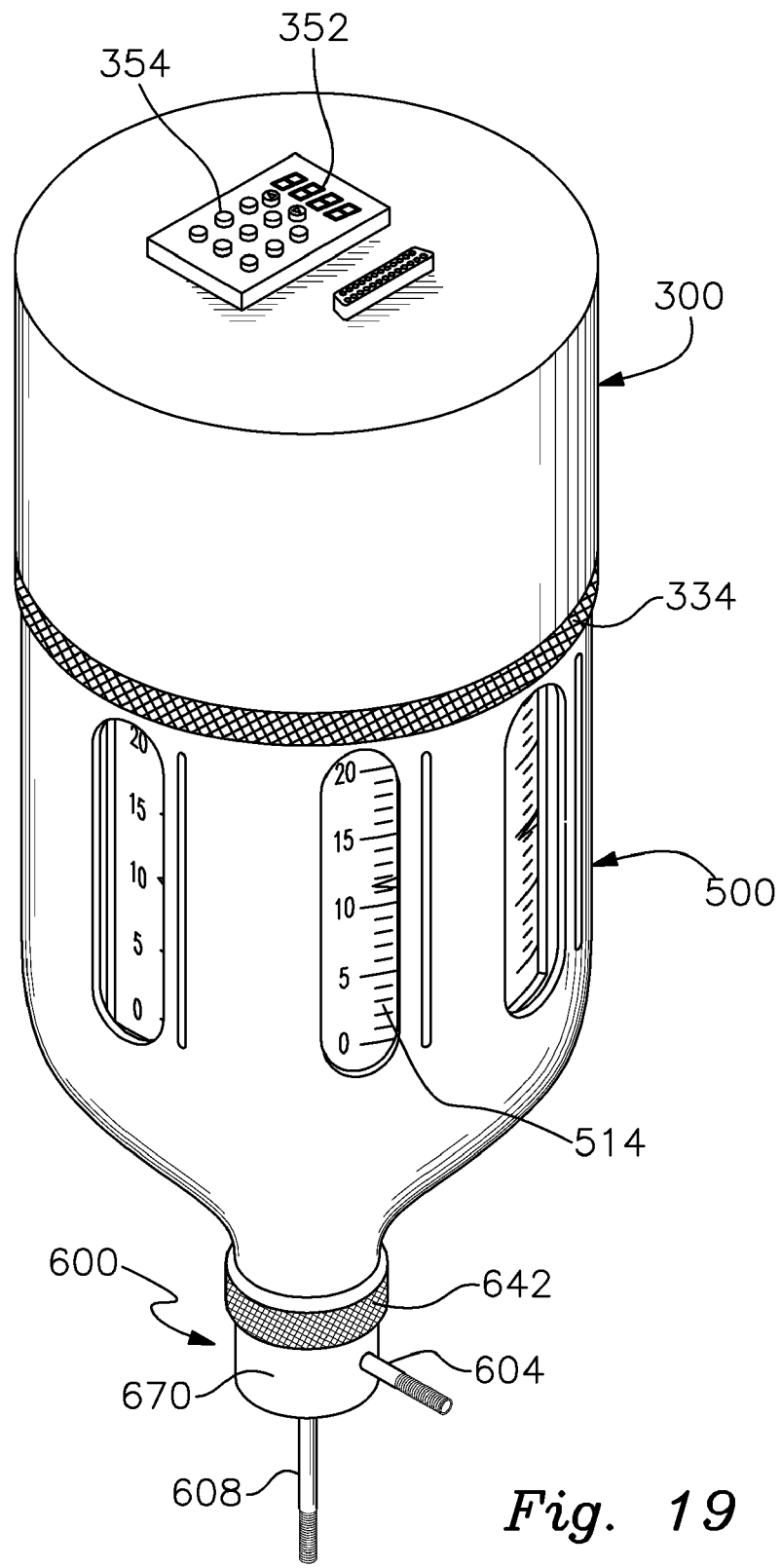
FIG. 19 shows a perspective view of an embodiment of the invention with an electronic head assembly.

Yet referring to FIG. 18, a sensor 320 is connected to said CPU 302 by a cable 318. Said sensor 320 is fixed relative to the case 301. A marker 322 is fixed onto the turntable 324. When said turntable 324 rotates the marker 322 past the sensor 320 an input into the CPU 302 is generated to calibrate the precise angular position of the turntable 324, and therefore necessarily the lineal actuator 328, relative to the case 301. The sensor 320 ensures that the plunger 332 is oriented directly over the proper vessel 514 (shown in FIG. 3) when the electronic head assembly 300 is attached to the case assembly 500 as shown in FIG. 19. The preferred embodiment of the sensor 320 is a Hall Effect Sensor with a magnet as the marker 322, but other sensors, such as a contact switch, would be equally effective.

FIG. 19 shows the assembled invention with the electronic head assembly 300. When the invention is in use the electronic head assembly 300 is secured to a case assembly 500 that is in turn connected to an apical assembly 600. The apical assembly as shown in FIGS. 13, 14 and 15 may be substituted for the apical assembly 600 when it is suitable to the application of the invention, for example when the invention is used to administer intra-muscular or intra-dermal injections.

Figure 20:
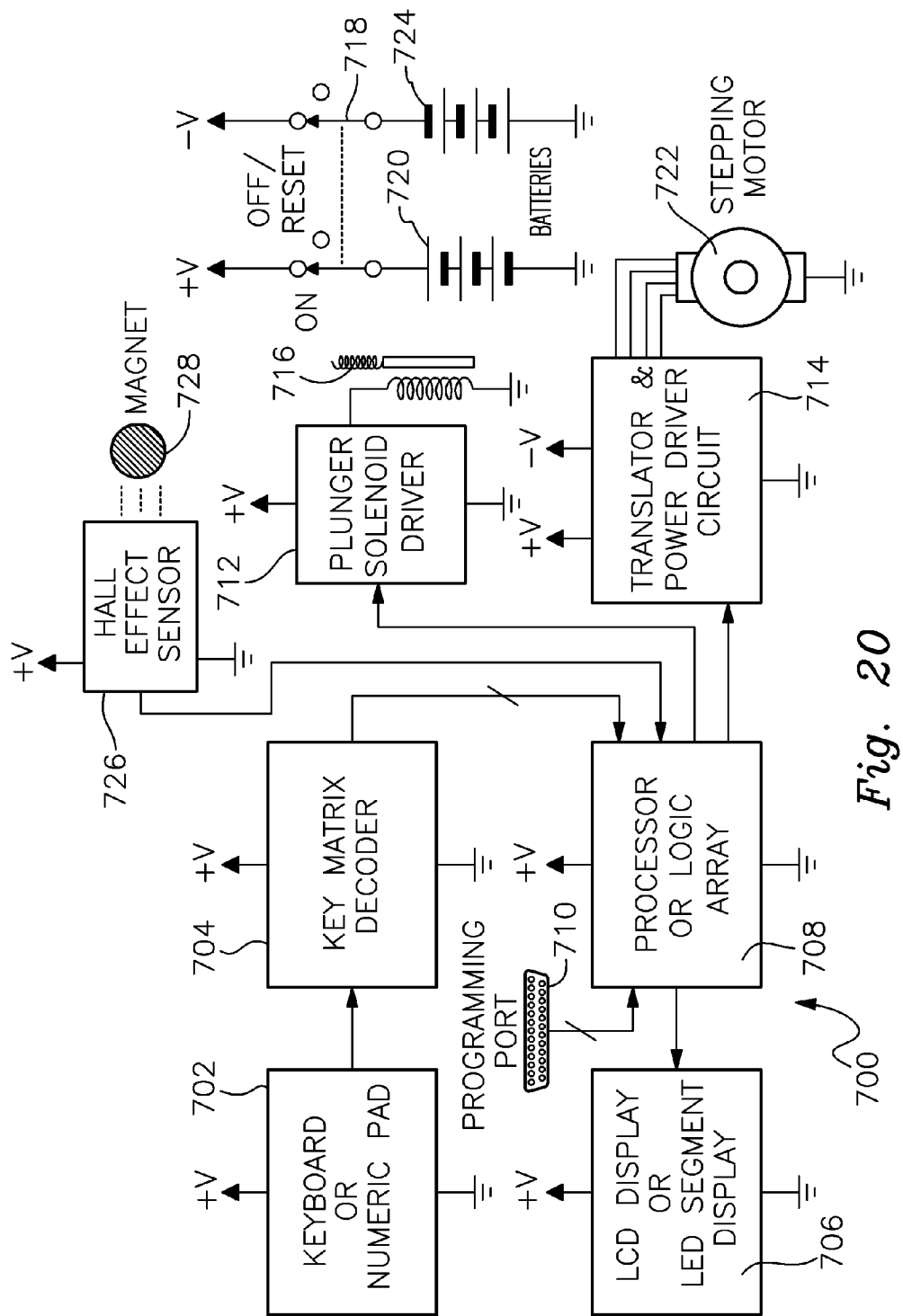
FIG. 20 is an example of a circuit diagram of an electrical head assembly.

FIG. 20 shows an example of a circuit configuration 700 utilized with, and contained inside, the electronic head assembly 300 as shown in FIG. 18. A processor 708 is the main controller and may also comprise a logic array and is powered by a battery 720. The circuit configuration 700 is powered up by switch 718. An input device 702 feeds user input through a decoder 704 into the processor 708. In the preferred embodiment the input device 702 may be, for example, a keyboard, numeric pad, buttons, switches or other commonly used input devices.

Said processor 708 optionally may also be connected to a port 710 to connect the circuit configuration 700 to an external computer that may perform such functions as programming, monitoring and/or controlling the circuit configuration 700.

A display 706 is optionally connected to the processor 708 to show information to the user such as the device status, fluid to be dispensed, fluid remaining, programming sequence, battery supply or any other relevant information.

Still referring to FIG. 20, a sensor 726 and marker 728 also provide an input into the processor 708 to aid in calibration of the position a lineal actuator 716 relative to the dispensed vessel 514 as described above in the discussion on FIG. 18 where sensor 320 is analogous to sensor 726, marker 322 is analogous to marker 728 and lineal actuator 328 is analogous to lineal actuator 716. In the preferred embodiment the sensor 726 is a Hall Effect Sensor that produces a signal when a magnet, shown as marker 728, passes next to the sensor 726. As an alternative, the sensor 726 may be a contact switch or other suitable means to indicate to the processor 708 when the sensor 726 is positioned next to the marker 728.

Said processor 708 gives input to a driver 714 that in turn activates a motor 722. In the preferred embodiment the motor 722 is a stepping motor. Said motor 722 is analogous to the motor 310 in FIG. 18 and performs to rotate the turntable 324 relative to the case 301, also shown in FIG. 18. In the preferred embodiment the driver 714 is a translator and power driver circuit. The driver 714 is connected to battery 720 with a positive potential to turn the motor in one direction and also connected to battery 724 with a negative potential to turn the motor 722 in the opposite direction.

Said processor 708 also controls a driver 712 that in turn activates a lineal actuator 716 as also shown in FIG. 18 as the lineal actuator 328. As described in the discussion on FIG. 18, above, the lineal actuator 716 provides the force to dispense fluid contained in a vessel 514, as shown in FIG. 3, when the shaft 330 and plunger 332, as shown in FIG. 18, extend and press upon the piston 524, as shown in FIG. 3.

Figure 21:
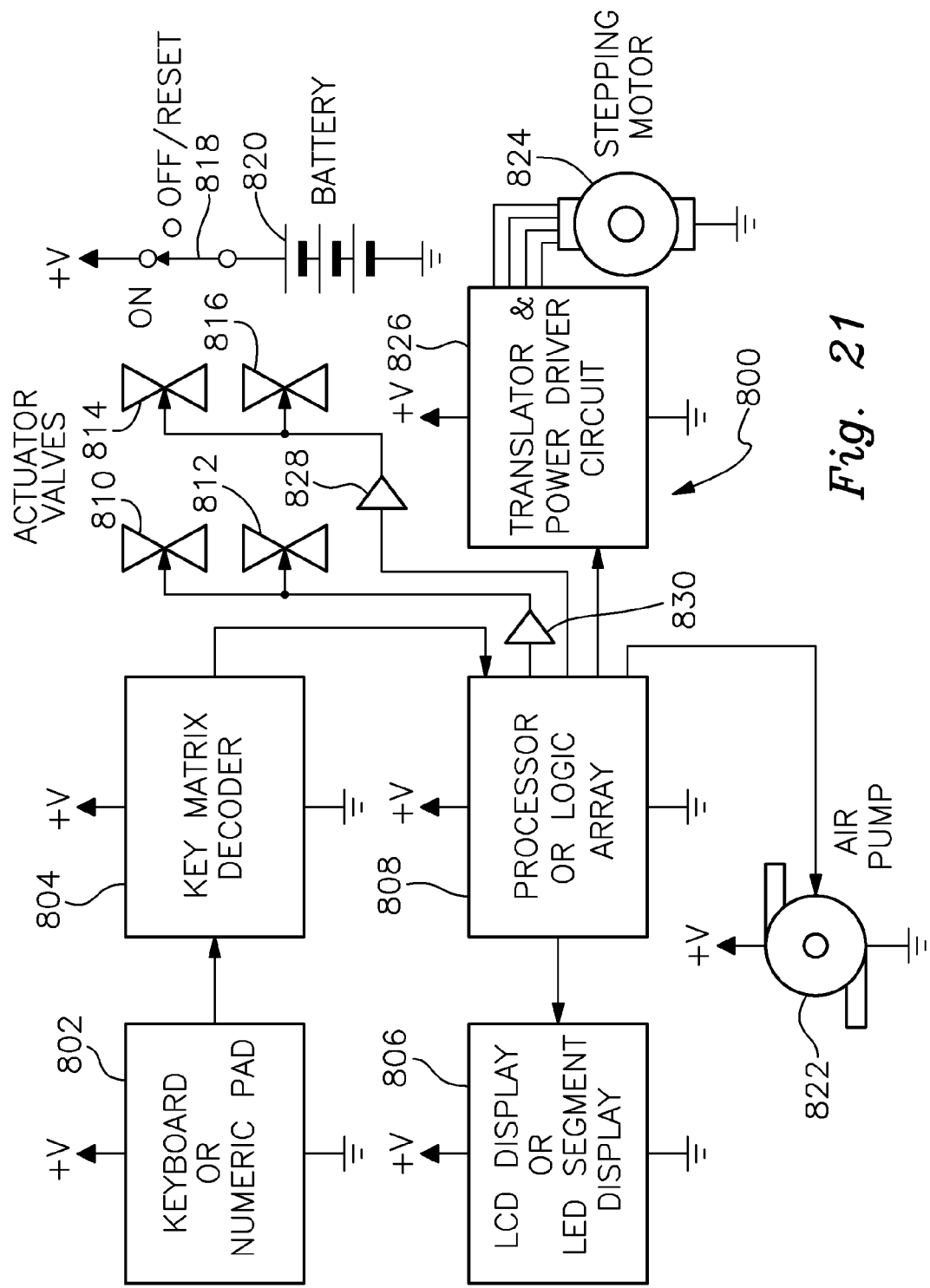
FIG. 21 is an example of a circuit diagram of a pneumatic head assembly.

Now referring to FIG. 21 that shows a circuit configuration 800 for the pneumatic head assembly 400, as shown in FIG. 16 and described above. Said circuit configuration 800 is typically contained inside the pneumatic head assembly 400 as shown in FIG. 16. A processor 808 is the main controller and may also comprise a logic array and is powered by a battery 820. The circuit configuration 800 is powered up by switch 818. An input device 802 feeds user input through a decoder 804 into the processor 808. In the preferred embodiment the input device 802 may be, for example, a keyboard, numeric pad, buttons, switches or other commonly used input devices.

Said processor 808 optionally may also be connected to a port (not depicted) to connect the circuit configuration 800 to an external computer that may perform such functions as programming, monitoring and/or controlling the circuit configuration 800, similar to port 710 described in the discussion of FIG. 20, above.

A display 806 is optionally connected to the processor 808 to show information to the user such as the device status, fluid to be dispensed, fluid remaining, programming sequence, battery supply or any other relevant information.

Still referring to FIG. 21, a sensor and marker (neither depicted in FIG. 21) similar to the sensor 320 and marker 322 shown on the electronic head assembly 300 as shown in FIG. 18 and described above may also be present to aid in calibration of the invention. In the preferred embodiment the sensor 320 is a Hall Effect Sensor that produces a signal when a magnet, shown as marker 322, passes next to the sensor 320. As an alternative, the sensor 320 may be a contact switch or other suitable means to indicate to the processor 808 when the sensor 320 is positioned next to the marker 322.

Said processor 808 gives input to a driver 826 that in turn activates a motor 824. In the preferred embodiment the motor 824 is a stepping motor. Said motor 824 is analogous to the motor 426 in FIG. 16 and performs to rotate the turntable 404 relative to the case 402, also shown in FIG. 16. In the preferred embodiment the driver 826 is a translator and power driver circuit. The driver 826 is connected to battery 820.

Said processor 708 also controls a driver 828 and a driver 830. Said driver 828 operates to either close or open both a valve 814 and a valve 816 simultaneously. Said valve 814 and said valve 816 are analogous to valve 416 and valve 434, respectively, shown in FIG. 17. Said driver 830 operates to close or open both a valve 810 and a valve 812 simultaneously. Said valve 810 and valve 812 are analogous to valve 418 and valve 436, respectively, shown in FIG. 17. Valve 810, valve 812, valve 814 and valve 816 operate in concert as described for the respective valves as shown in FIG. 17 and described above in the discussion on FIG. 17 to move said piston 468, shaft 440 and plunger 442 up and down.

Said circuit configuration 800 includes a pump 822 to supply a pressure source as an alternative to the pressure vessel 446 as shown in FIG. 17. The pump 822 supplies a pressure greater than ambient pressure to valve 814 and valve 812.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An anesthesia medication dispensing device comprising:
    A) a head assembly comprising a case having a base, said case housing a turntable that is rotatable relative to said base, said turntable has a cylinder mounted thereon, said cylinder having a shaft extending therefrom that terminates as a plunger, said shaft retractably extends through and below said turntable, said head assembly also comprising selecting means to select a fluid medication to be dispensed and dispensing means to dispense said fluid medication, said selecting means comprises an input device that sends input to a central processing unit, said dispensing means is pneumatically powered by a pressure vessel housed within said case, said dispensing means causes said plunger to apply a force onto a plurality of pistons, said turntable has a plurality of teeth around its periphery, and in addition a force for rotating said turntable is provided by a motor;
    B) a case assembly that contains a removable cartridge of multiple said fluid medication to be dispensed, said removable cartridge comprises said plurality of pistons, said plurality of pistons have a respective plurality of vessels with vessel ports by which said fluid medication travels through;
    C) an apical assembly comprising an apical cap and an apical cartridge assembly housed therein, said apical cartridge assembly comprising a plurality of septum that each correspond to their said respective plurality of vessels with vessel ports, said apical assembly funnels said fluid medication through a common output, said apical assembly further having a port for an external intravenous fluid source to continuously flush along an entire length of an apical chamber of the apical assembly to prevent comingling of said fluid medication; and
    D) said dispensing means to dispense said fluid medication having a mechanical means to limit volume of said fluid medication dispensed.

2. The anesthesia medication dispensing device set forth in claim 1, further characterized in that said central processing unit controls said selecting means to select said fluid medication to be dispensed and said dispensing means to dispense said fluid medication.

3. The anesthesia medication dispensing device set forth in claim 2, where said head assembly, said case assembly and said apical assembly are separable.

4. The anesthesia medication dispensing device set forth in claim 3, further characterized in that said external intravenous fluid is a sterile saline solution.

5. An anesthesia medication dispensing device consisting of:
  A) a head assembly comprising a case having a base, said case housing a turntable that is rotatable relative to said base, said turntable has a cylinder mounted thereon, said cylinder having a shaft extending therefrom that terminates as a plunger, said shaft retractably extends through and below said turntable, said head assembly also comprising selecting means to select a fluid medication to be dispensed and dispensing means to dispense said fluid medication, said selecting means comprises an input device that sends input to a central processing unit, said dispensing means is pneumatically powered by a pressure vessel housed within said case, said dispensing means causes said plunger to apply a force onto a plurality of pistons, said central processing unit controls said selecting means to select said fluid medication to be dispensed and said dispensing means to dispense said fluid medication, said turntable has a plurality of teeth around its periphery, and in addition a force for rotating said turntable is provided by a motor;
  B) a case assembly that contains a removable cartridge of multiple said fluid medication to be dispensed, said removable cartridge comprises said plurality of pistons, said plurality of pistons have a respective plurality of vessels with vessel ports by which said fluid medication travels through;
  C) an apical assembly comprising an apical cap and an apical cartridge assembly housed therein, said apical cartridge assembly comprising a plurality of septum that each correspond to their said respective plurality of vessels with vessel ports, said apical assembly funnels said fluid medication through a common output, said apical assembly further having a port for an external intravenous fluid source to continuously flush along an entire length of an apical chamber of the apical assembly to prevent comingling of said fluid medication, said head assembly, said case assembly and said apical assembly are separable; and
  D) said dispensing means to dispense said fluid medication having a mechanical means to limit volume of said fluid medication dispensed, said external intravenous fluid is a sterile saline solution.

* * * * *

UNITED STATES PATENT AND TRADEMARK OFFICE
CERTIFICATE OF CORRECTION

PATENT NO. : 7,935,086 B2  Page 1 of 1
APPLICATION NO. : 11/610930
DATED : May 3, 2011
INVENTOR(S) : John P. Lafferty, IV It is certified that error appears in the above-identified patent and that said Letters Patent is hereby corrected as shown below:

Title Page Item [73] should read
ASSIGNEE: L M M Global Innovations, Inc.
ASSIGNEE ADDRESS: 11660 Canal Drive, Suite B, North Miami, FL 33181

Signed and Sealed this
Seventh Day of June, 2011

David J. Kappos
*Director of the United States Patent and Trademark Office*